United States Patent
Shrivastava

(10) Patent No.: US 11,192,102 B2
(45) Date of Patent: Dec. 7, 2021

(54) MICROFLUIDIC DEVICE

(71) Applicant: LMSERA INC., Sidney (CA)

(72) Inventor: Sanjiv Shrivastava, Sidney (CA)

(73) Assignee: LMSERA INC., Sidney (CA)

( * ) Notice: Subject to any disclaimer, the term of this patent is extended or adjusted under 35 U.S.C. 154(b) by 0 days.

(21) Appl. No.: 16/488,023

(22) PCT Filed: Feb. 28, 2018

(86) PCT No.: PCT/CA2018/050231
§ 371 (c)(1),
(2) Date: Aug. 22, 2019

(87) PCT Pub. No.: WO2018/157245
PCT Pub. Date: Sep. 7, 2018

(65) Prior Publication Data
US 2019/0374947 A1    Dec. 12, 2019

Related U.S. Application Data

(60) Provisional application No. 62/464,602, filed on Feb. 28, 2017.

(51) Int. Cl.
*B01L 3/00* (2006.01)
*G01N 33/543* (2006.01)
*G01N 33/48* (2006.01)

(52) U.S. Cl.
CPC ... *B01L 3/502715* (2013.01); *B01L 3/502761* (2013.01); *G01N 33/54366* (2013.01);
(Continued)

(58) Field of Classification Search
CPC ......... B01L 3/502715; B01L 3/502761; B01L 3/5027; B01L 3/502; B01L 3/50;
(Continued)

(56) References Cited

U.S. PATENT DOCUMENTS

| | | | |
|---|---|---|---|
| 2003/0138941 A1* | 7/2003 | Gong | B01L 3/5027 435/287.2 |
| 2003/0156993 A1* | 8/2003 | Staats | G01N 30/92 204/455 |

(Continued)

FOREIGN PATENT DOCUMENTS

WO    2007041619 A2    4/2007

OTHER PUBLICATIONS

Castellana, Direct Writing of Metal Nanoparticle Films Inside Sealed Microfluidic Channels, Anal. Chem., 2006, 78, 107-112. (Year: 2006).*

(Continued)

*Primary Examiner* — Christine T Mui

(57) ABSTRACT

A microfluidic device for the separation and immobilization of one or more cells into sample wells based on one or more physical properties of the one or more cells is provided. Metallic film or magnets are positioned on or below the wells. Openings in the device above the sample wells accommodate a measurement system to determine one or more physical characteristics or properties of the one or more cells immobilized within the microfluidic device. A method for determining a property or one or more physical characteristics of the immobilized one or more cells is also provided.

21 Claims, 13 Drawing Sheets

(52) U.S. Cl.
CPC .......... *B01L 2200/0652* (2013.01); *B01L 2300/0636* (2013.01); *B01L 2300/0681* (2013.01); *B01L 2300/0816* (2013.01); *B01L 2300/0851* (2013.01); *B01L 2300/0858* (2013.01); *B01L 2300/0864* (2013.01); *B01L 2400/043* (2013.01)

(58) Field of Classification Search
CPC ..... B01L 2200/0652; B01L 2300/0636; G01N 33/54366; G01N 33/54313; G01N 33/543; G01N 33/53
USPC .......................................... 422/502, 500, 50
See application file for complete search history.

(56) References Cited

U.S. PATENT DOCUMENTS

| | | | |
|---|---|---|---|
| 2005/0106066 A1* | 5/2005 | Saltsman | F04B 43/043 422/504 |
| 2005/0274650 A1 | 12/2005 | Frazier et al. | |
| 2006/0134599 A1 | 6/2006 | Toner et al. | |
| 2007/0184463 A1* | 8/2007 | Molho | G01N 1/34 435/6.19 |
| 2010/0039919 A1 | 2/2010 | Chou et al. | |
| 2013/0130232 A1* | 5/2013 | Weibel | B01L 3/50273 435/5 |
| 2015/0047078 A1 | 2/2015 | Sarkar et al. | |

OTHER PUBLICATIONS

Cappella, B. et al., "Force-distance curves by atomic force microscopy", Service Science Reports, vol. 34, 1999, pp. 1-104.
Dukic, M. et al., "Piezoresistive AFM cantilevers surpassing standard optical beam deflection in low noise topograpy imaging", Science Reports, 2015, 11 pages.
Han, K-H et al., "A Microfluidic System for Continuous Magnetophoretic Separation of Suspended Cells Using Their Native Magnetic Properties", NSTI-Nanotech, vol. 1, 2005, 4 pages.
Iliescu, C. et al., "Microfluidic Device for Continuous Magnetophoretic Separation of Red Blood Cells", HAL-00277724, DTIP of MEMS & MOEMS 9-11, 2008, 4 pages.
Inglis, D.W. et al., Microfluidic high gradient magnetic cell separation, Journal of Applied Physics 99, 08K101, 2006, 3 pages.
Ngan, A.H.W. et al., "Response of power-law-viscoelastic and time-dependent materials to rate jumps", J. Mater. Res. vol. 24, No. 3, 2009, 10 pages.
Wu, W-T et al., "Design of microfluidic channels for magnetic separatin of malaria-infected red blood cells", HHS Public Access, Microfluid Nanofluidics 20(2), 2016, 27 pages.
Furlani, E.P., "Continuous Magnetophorectic Separation of Blood Cells from Plasma at the Microscale", 2007, 28 pages.
Vettiger, P. et al., The "Millipede"—Nanotechnology Entering Data Storage, IEEE Transactions On Nanotechnology, vol. 1, No. 1, 2002, 17 pages.
Butt, H-J et al., "Force measurements with the atomic force microscope: Technique, interpretation and applications", Science Direct, Surface Science Reports, vol. 59, 2005, pp. 1-152.

* cited by examiner

MICROFLUIDIC DEVICE

FIELD OF INVENTION

The present invention relates to a microfluidic device and method for isolating and immobilizing cells in vitro.

BACKGROUND OF THE INVENTION

Many clinical and molecular diagnostic tests require the in vitro separation of blood cells from samples of whole blood. Conventional methods of cell separation can provide high efficiency sorting by exploiting various physical properties of cells. For example, cells may be separated based on their size, density, expression of specific cell surface proteins, or, as in the particular case of red blood cells (RBCs), magnetic properties. Cell separation has also been achieved using advances in microfluidic technology, which enable precise physical and temporal handling of blood samples in a miniaturized scale, for example as described in US 2006/0134599. Microfluidic devices also facilitate the ability to perform multiple processing or analytical steps on an integrated platform for complete "lab-on-a-chip" applications.

Methods of separating RBCs from whole blood samples have been developed that do not require the use of exogenous labelling techniques, instead relying on the inherent magnetic properties of RBCs. RBCs are magnetic due to their high content of hemoglobin. Hemoglobin is a protein comprising of four polypeptide chains, each of which contains a central iron atom capable of reversibly binding oxygen. In its deoxygenated form, each of hemoglobin's iron atoms contains four unpaired electrons, giving the protein a paramagnetic moment.

Frazier and Han (US 2005/0274650; Han, K. and A. B. Frazier, NSTI-Nanotech 2005, Vol 1, 2005, pg 187-190) disclose a single stage and cascaded stage microseparator that separates RBCs from whole blood using a high gradient magnetic field. The high gradient magnetic field is generated when an external magnetic field is applied normal to the axis of a microfluidic channel having a small ferromagnetic wire disposed along its length. Blood cells flowing parallel to the ferromagnetic wire experience a magnetic force, whereby RBCs are forced away from the magnetic wire and into an outlet channel, while WBCs are drawn closer to the ferromagnetic wire and forced into a second separate outlet channel. This device may be configured to operate in a paramagnetic capture mode, where an external magnetic field is applied perpendicular to the ferromagnetic wire, causing RBCs to be drawn closer to the ferromagnetic wire and WBCs forced away from the magnetic wire.

Inglis et al. (J. App. Phys. 99, 08K10, 2006) teach a device using magnetic stripes recessed into a silicon substrate to alter the flow of cells comprising antibody-conjugated magnetic beads. The stripes were magnetized by an externally applied magnetic field, causing the labeled cells to be attracted to the stripes and follow the direction of the stripes. A similar method using a microfluidic device for separating cells using magnetically labeled target analytes is described in US 2004/0018611.

Iliescu et al. (DTIP 2008, April 2008, Nice, France. EDA PUBLISHING Association, pp. 279-281, 2008) describe a microfluidic device for extraction of RBCs from blood under a continuous flow. The device consists of a glass microfluidic channel with ferromagnetic "dots" embedded on its bottom. When an external magnetic field is applied perpendicular to the flow of direction of blood sample, a magnetic force is generated which acts on the hemoglobin-rich RBCs, thereby drawing them to the bottom of the microfluidic channel, permitting white blood cells (WBCs) to be flushed out along with other blood components.

SUMMARY OF THE INVENTION

The present invention relates to a microfluidic device and method for isolating and immobilizing cells from heterogeneous cell populations in vitro.

It is an object of the invention to provide an improved, microfluidic device.

As described herein there is are methods and devices for separating and immobilizing cells from a sample using a microfluidic device, wherein the separation is based on properties of the cell. The properties may include, for example, cell size, cell magnetic moment, expression of cell surface molecules, conjugated magnetic beads, or a combination thereof. The methods and devices described herein also permit immobilization of the cell to a specific location within the microfluidic device to facilitate the precise measuring of the cell's physical properties.

An example of a sample may be a blood sample, and the cell that is immobilized and separated is a blood cell, for example, a red blood cell. If the sample is a blood sample, then the microfluidic device may be termed a blood sample cartridge.

As described herein there is provided a microfluidic device comprising a sample inlet, an optional cell selective filter, and a cell retention body. The cell retention body comprises one or more than one microchannel in fluid communication with the sample inlet. Each of the one or more than one microchannel further comprises a lower first wall, an optional upper second wall, and side walls, the lower first, optional upper second and side walls defining a microchannel volume. The lower first wall comprises one or more than one sample well along a length of the microchannel and each sample well further comprises a sample well base, one or more than one sample well side wall, and a metallic film positioned on or below the sample well base. The optional upper second wall of the microchannel defines one or more than one opening so that each opening is in spatial alignment, and positioned above, each of the one or more than one sample well.

Each of the one or more than one opening of the optional upper second wall in the microfluidic device described above provides access of a measurement system, an observation probe, or an optical microscope, that may be used for measuring one or more than one physical or biochemical property, for example, an electrical property, an electrical conductivity, an electrical resistivity, a magnetic property, an acoustic property, a mechanical property, an elastic property, a viscoelastic property, a viscosity property, a shear force property, a torsion property, a hardness property, an optical property, a thermal property, pH, or a combination of one or more of the properties of a cell, or a membrane of a cell when located within the one or more than one sample well. A non-limiting example of the cell is a red blood cell. Non-limiting examples of a measurement system include a near-surface probe having nanometer-or micron scale resolution, a proximity surface probe, a displacement probe, a magnetic probe, a load sensor probe, a thermal probe, a scanning probe-based microscope (SPM), an atomic force microscope (AFM), a torsion or lateral force microscope, a sliding AFM probe, a piezoresistive cantilever, a digital camera, or an indenter. If the microfluidic device does not comprise the optional second wall, then the measurement system, observation probe, or optical microscope, that is positioned above and in spatial alignment with the one or more than one sample well, may have direct access to the one or more than one sample well, and to a cell, when the cell is located within the one or more than one sample well.

The sample inlet of the microfluidic device as described above, may comprise a first opening for receiving a sample, for example, a sample of blood, a second opening for receiving diluent, and a mixing chamber in which the sample and diluent are mixed. Alternatively, the sample inlet may comprise one opening for receiving the sample, or the sample inlet may comprise a pre-loaded reservoir of diluent, one opening for receiving the sample, and a mixing chamber in which the sample is mixed with the diluent. The one or more than one microchannel may be in fluid communication with a flow-through collection reservoir. Furthermore, the flow through collection reservoir may further comprise an absorber to facilitate flow of the sample through the microchannel and into the collection reservoir.

The microchannel side walls of the microfluidic device as described in (A) or (B) above may have a height between about 1.0 μm and about 30.0 μm. Furthermore, the one or more than one sample well base may be circular in shape with a diameter between about 8.0 μm and about 30.0 μm and the sample well side wall may be curved or sloped.

In the microfluidic device as described above, the metallic film of the sample well may be comprised of nickel, cobalt, platinum, graphene, graphene spiked with metallic or conductive components, neodymium-iron-boron, niobium-iridium-iron, silver, gold, CVD. Additionally, a magnet may be located immediately below each of the one or more than one sample wells so that the metallic film serves to concentrate the magnetic field generated by the magnet at each of the one or more than one sample wells.

Also provided herein is a microfluidic device as described above, wherein each of the one or more than one sample well base is coated with cell-specific binding molecules.

A method for separating one or more than one target cell from a sample is also provided. The method comprises applying a magnetic field to a microfluidic device, the microfluidic device comprising a sample inlet, an optional cell selective filter, and a cell retention body, the cell retention body comprising one or more than one microchannel in fluid communication with the sample inlet, each of the one or more than one microchannel comprises a lower first wall, an optional upper second wall, and side walls, the lower first, upper second and side walls defining a microchannel volume, the lower first wall comprises one or more than one sample well along a length of the microchannel, each of the one or more than one sample well comprises a sample well base, one or more than one sample well side wall and a metallic film positioned on or below the sample well base, the optional upper second wall may define one or more than one opening so that each of the one or more than one opening is in spatial alignment, and positioned above, each of the one or more than one sample well, and introducing the sample containing the one or more than one target cell into the sample inlet of the microfluidic device, and permitting the sample to flow along the one or more than one microchannel so that one of the one or more than one target cell is retained within the one or more than one sample well, thereby separating the one or more than one target cell from the sample to produce a separate target cell.

A method of determining a property of a cell is also described. The method comprises, producing a separated target cell by the method described above, and determining one or more than one physical or biochemical property, for example, an electrical property, an electrical conductivity, an electrical resistivity, a magnetic property, an acoustic property, a mechanical property, an elastic property, a viscoelastic property, a viscosity property, a shear force property, a torsion property, a hardness property, an optical property, a thermal property, pH, or a combination of the properties of the separated target cell, or a membrane of the separated target cell.

The microfluidic device as described herein selectively separates one or more than one cell (a target cell) from a sample, and registers each of the separated one or more than one cell within a sample well of the microfluidic device. By using both physical and magnetic parameters, the microfluidic device described herein efficiently separates and retains a target cell from a heterogeneous sample. The separated target cell is retained within the sample well thereby permitting analysis of the separated target cell using physical, biochemical, or a combination thereof techniques.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1A:
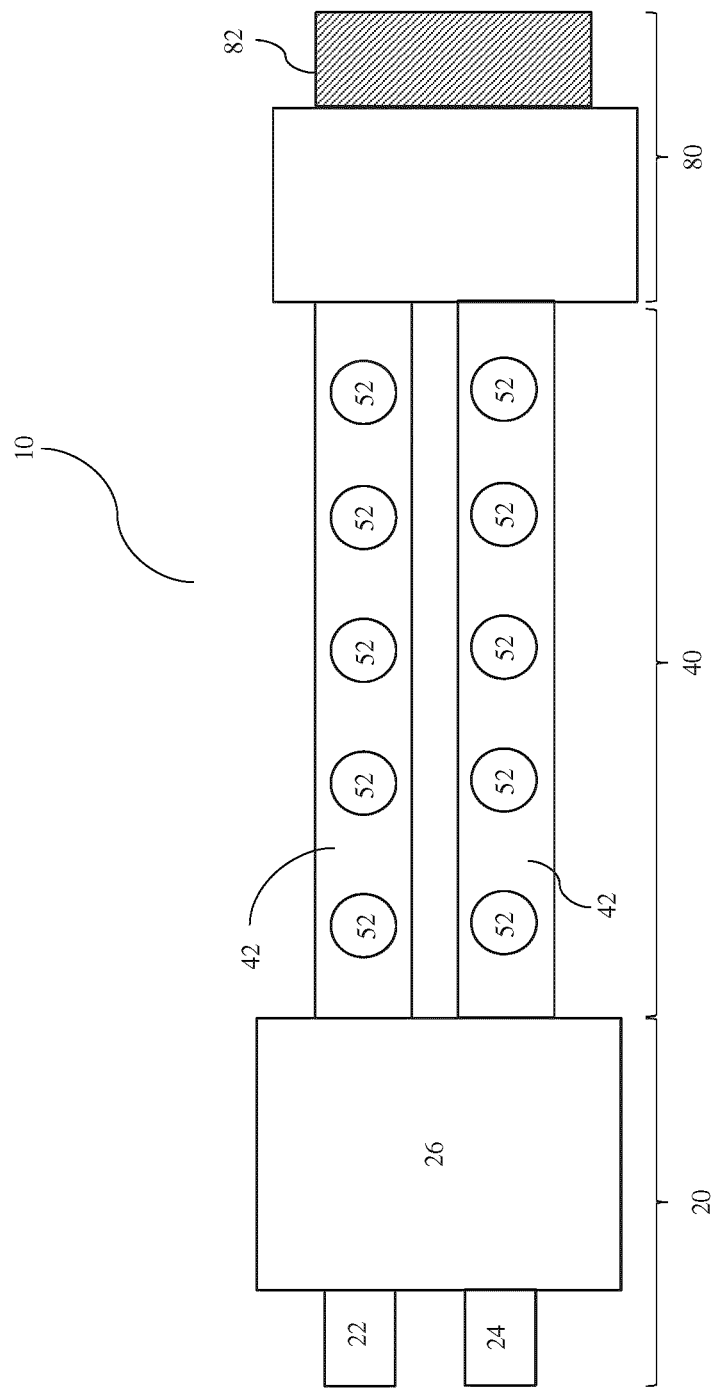
FIG. 1A shows a top view of a non-limiting example of a microfluidic device (10) as described herein.

The present invention relates to a microfluidic device and method for the isolation and immobilization of cells. For example, the microfluidic devices and methods described herein may be used to separate red blood cells (RBCs) from a blood sample and register the separated red blood cells in defined locations within the microfluidic device for further analysis.

The following description is of a preferred embodiment.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The microfluidic device as described herein generally comprises a sample inlet for receiving a sample comprising cells, for example but not limited to, a blood sample, an optional cell selective filter, and a cell retention body for the isolation and immobilization of a specific number of cells within the device. Once isolated and immobilized, the cells are positioned in defined locations within the retention body so that further analysis of the cells may be conducted. Further analysis may comprise determining one or more physical or biochemical measurements of each separated, immobilized cell, for example determining a physical property of the membrane of the immobilized cell, for example, an electrical property, an electrical conductivity, an electrical resistivity, a magnetic property, an acoustic property, an optical property, a mechanical property, an elastic property, a viscoelastic property, a viscosity property, a shear force property, a torsion property, a hardness property, an optical property, a thermal property, pH or a combination of these properties using a near-surface probe having nanometer-or sub-micron scale resolution, a proximity surface probe, a displacement or load sensor probe, a magnetic probe, an optical microscope, a digital camera, a scanning probe-based microscope (SPM), an atomic force microscope (AFM), a sliding AFM probe, torsion or lateral fore microscope, a piezoresistive cantilever (with Z-movement of the cantilever tip to determine an elastic modulus measurement of the membrane of the isolated, immobilized cell), a nanometer scale resolution form of scanning probe microscopy, an "indenter" (for measuring the hardness of a substance through the use of displacement and load sensors), or using near surface sensor based technique, for example, using an acoustic-probe or a thermal-probe.

Alternatively, one or more biochemical properties of each separated, immobilized cell may be determined, for example, using ELISA analysis, biomarker analysis and the like. Furthermore, if desired, the separated cell may be chemically treated or lysed for analysis of cytoplasmic contents using methods that are known within the art.

The sample that is to be separated using the device as described herein may comprise any type of cell, for example, a red blood cell, a cell culture, or other cell preparation where each of the cells are free-floating and separable based on physical, magnetic or biochemical properties. If the cell does not exhibit any inherent magnetic properties, then the cell can be conjugated so that it acquires an introduced magnetic property, for example, using conjugated magnetic beads as is known in the art (e.g. Inglis et al. J. App. Phys. 99, 08K10, 2006).

By the term "blood cell", it is meant cells found in circulating whole blood including: red blood cells, neutrophils, eosinophils, mast cells, basophils, monocytes, megakaryocytes, T-cells and B-cells. Red blood cells are well suited for separation as described herein since they are biconcave discs, about 8.5 um in diameter and about 2.4 um thick. RBCs have the capacity to align with the direction of flow along the microchannel, and they are flexible and will deform and extend under shear forces. The normal range for the viscosity of human plasma is about 1.25+/−0.10 mPa·s at 37 degC, and the mean red cell volume (MCV) for healthy adults is 83 to 101 fl.

Examples of a microfluidic device as described herein are shown in FIGS. 1A, 1B, 2A-2E, 3 and 4. The microfluidic device 10 is comprised of a sample inlet 20, with an optional cell selective filter 30 (also see FIG. 1E), for receiving a sample comprising cells, for example a blood sample, a cell retention body 40 for isolating and immobilizing a number of cells within the cell retention body 40, and optionally, a flow-through collection reservoir 80 for collecting excess sample, flow-through fluid and/or non-retained cells. The microfluidic device 10 may be of any appropriate size and dimension (i.e. length, height, width) to suit a corresponding application. The microfluidic device 10 may also be configured as required to interact with a corresponding measuring device. Furthermore, the microfluidic device may comprise square edges as shown in the figures, or the microfluidic device may comprise alternate edge-configurations as desired, for example, rounded edges, chamfered edges and the like.

The sample inlet 20 comprises an opening 22 for receiving a droplet of the sample, for example, but not limited to a blood sample. The sample inlet 20 may comprise a filter 30, for example a cell selective filter, for example as shown in FIG. 1E. In the example shown in FIGS. 1A, 2D and 2E, the sample inlet 20 comprises two extensions or openings, one comprising opening 22 for receiving the sample, and the second, an optional opening 24 for receiving a volume of diluent. The sample inlet 20 may also comprise one extension or opening, and opening 22 and second opening 24 may be the same, as shown in FIG. 1B. If the sample inlet 20 comprises one opening, then the sample and the diluent (if used) are applied to the device though the same opening. The opening 22 and the second opening 24 may also be two separate openings located within the same extension of a sample inlet 20. Alternatively, the device may comprise a sample inlet 20 which is pre-filled with diluent, and the sample is added to the sample inlet 20 through opening 22 thereby permitting the sample to mix with the pre-loaded diluent. For example, the sample inlet 20 may comprise a reservoir which is pore-filled with diluent and upon addition of a sample to the microfluidic device 10, the diluent is mixed with the sample.

The use of a diluent within the microfluidic device is optional. For example, if the sample is a blood sample, then dilution of the blood sample with a diluent may assist in achieving optimal fluid flow through the microfluidic device 10, and for cell immobilization within the cell retention body 40. However, if the original sample is pre-diluted, or of a low enough viscosity that no further dilution is required to enable flow within microchannel 42, then the use of additional diluent may not be required. If a diluent is used, then the diluent may be any cell-compatible fluid, for example, a phosphate buffered saline (PBS) solution, a buffered solution, Ringers solution, a cell growth media and the like.

Figure 1B:
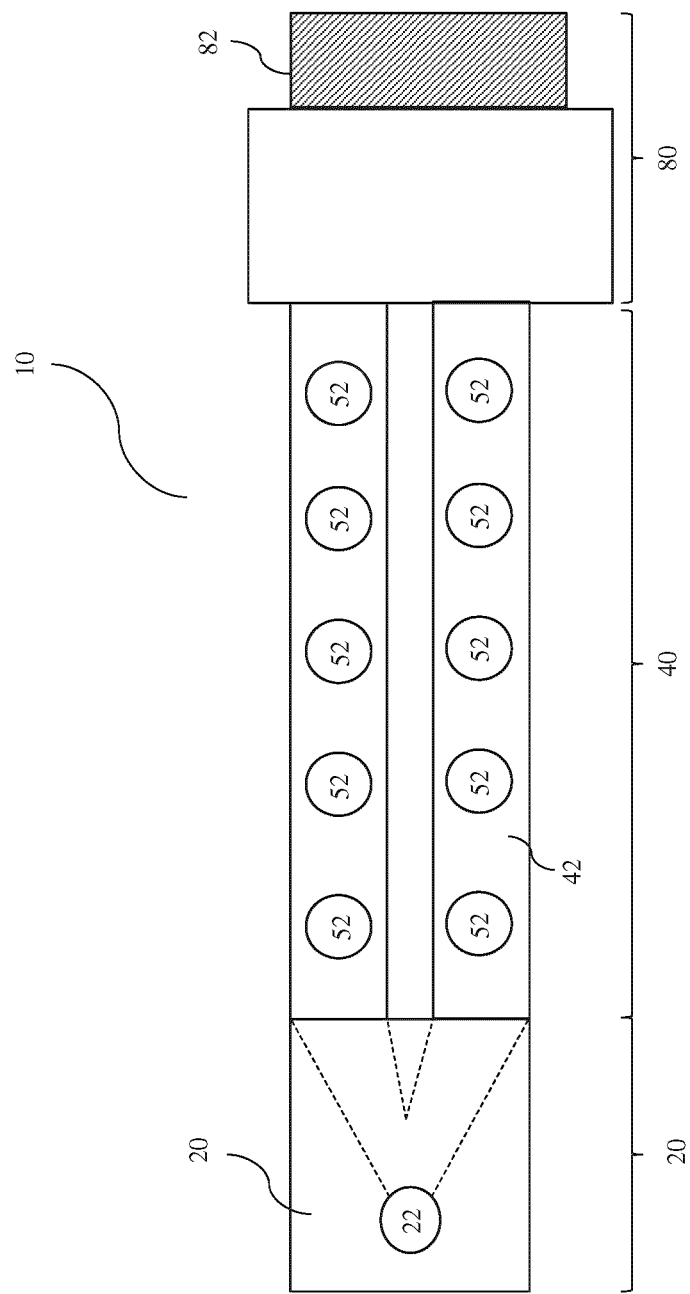
FIG. 1B shows a top view of an alternate example of a microfluidic device (10) as described herein.
Figure 1C:
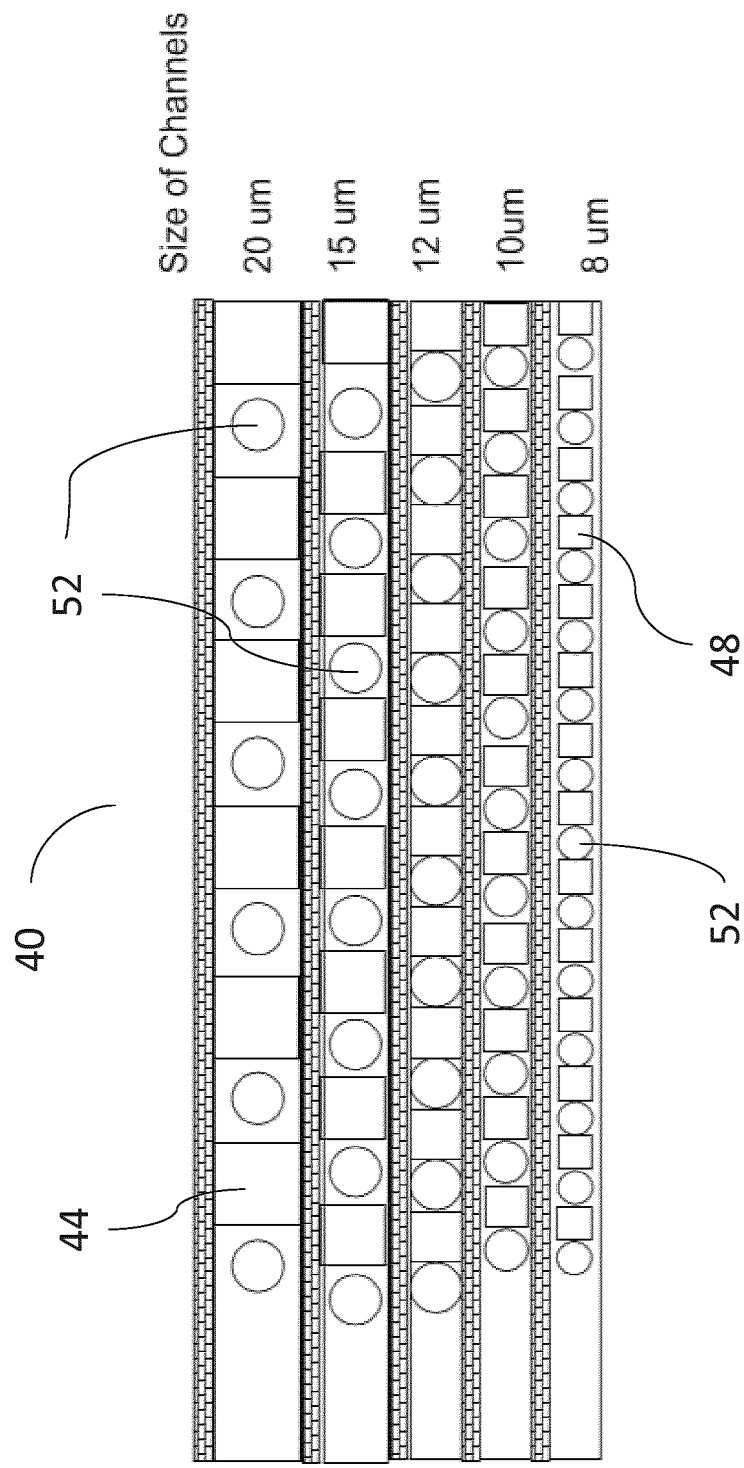
FIG. 1C shows a top view of a non-limiting example of a cell retention body (40) comprising a variety of microchannels (42) that range in width of from 8 μm to about 30 μm, and, in this example, sample wells (52) with diameters that range from about 8 μm to about 20 μm within the microchannels. As described herein the diameters of sample may range from about 8 to about 30 μm.
Figure 1D:
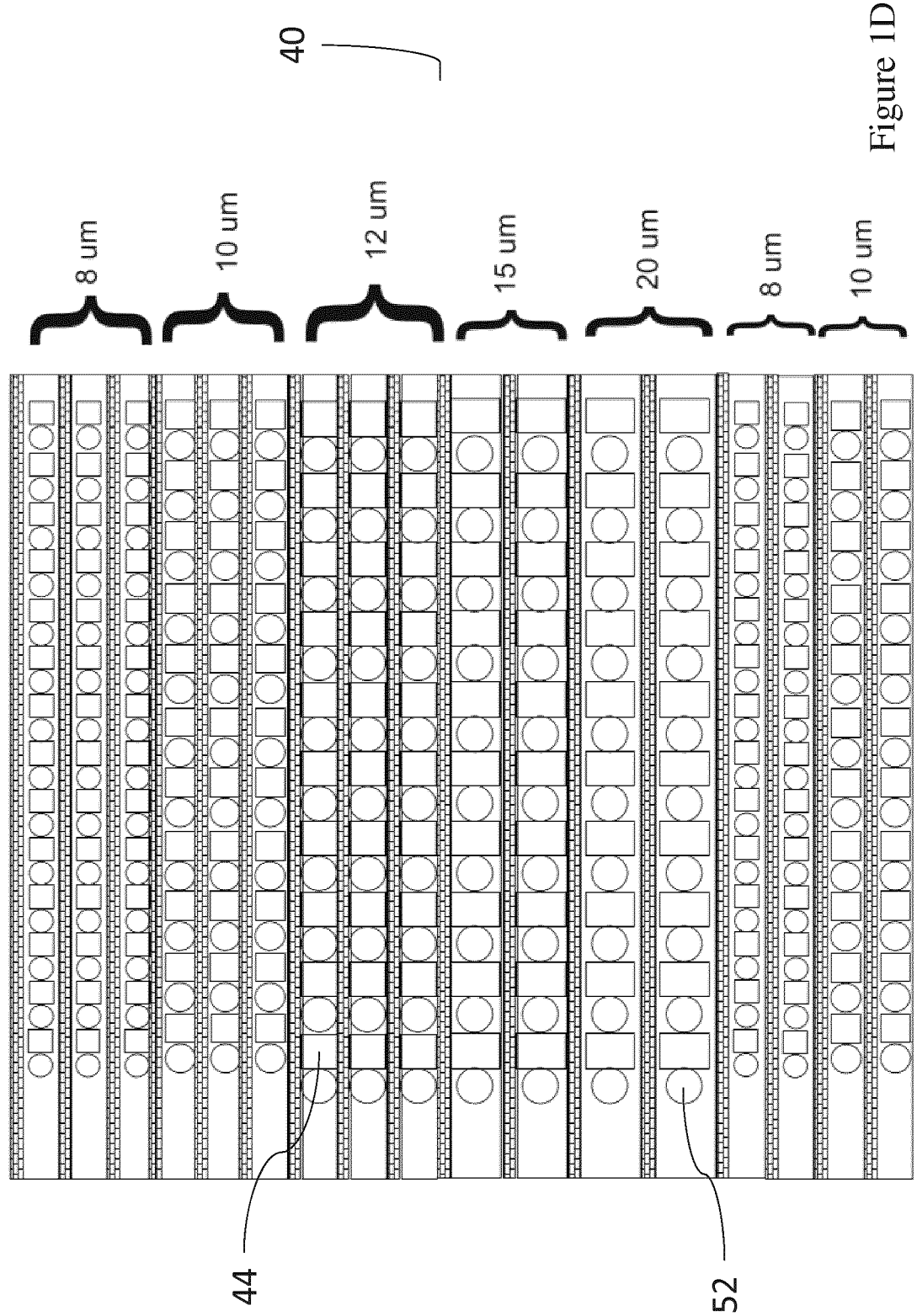
FIG. 1D shows a top view of another non-limiting example of a cell retention body (40) comprising a variety of microchannels (42) that range in width of from 8 μm to about 30 μm, and in this example, sample wells (52) with diameters that range from about 8 μm to about 20 μm within the microchannels. As described herein the diameters of sample may range from about 8 to about 30 μm.
Figure 1E:
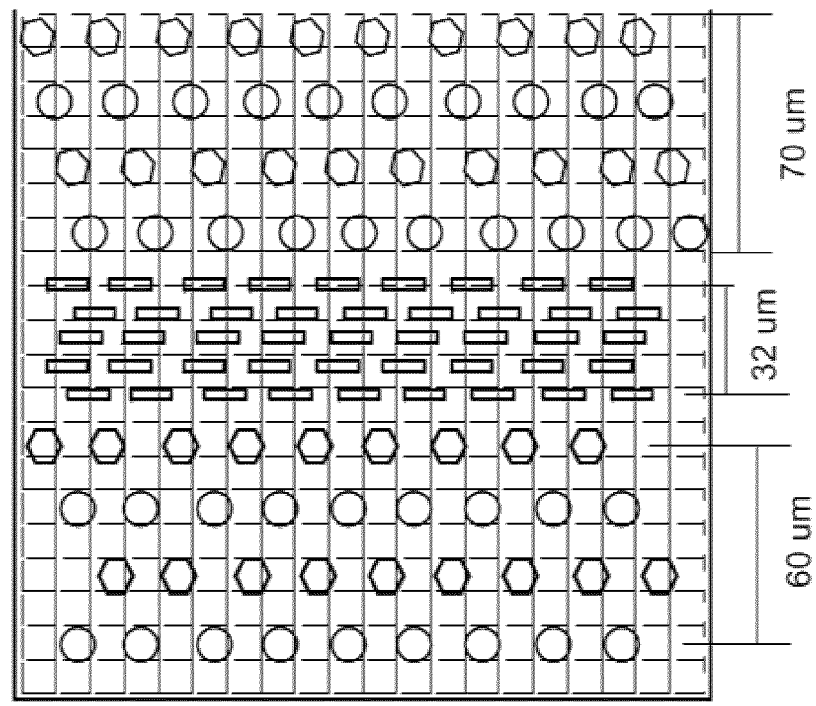
FIG. 1E shows a non-limiting example of a cell selective filter (30) comprising opens and perforations of a variety of sizes and shapes.
Figure 2A:
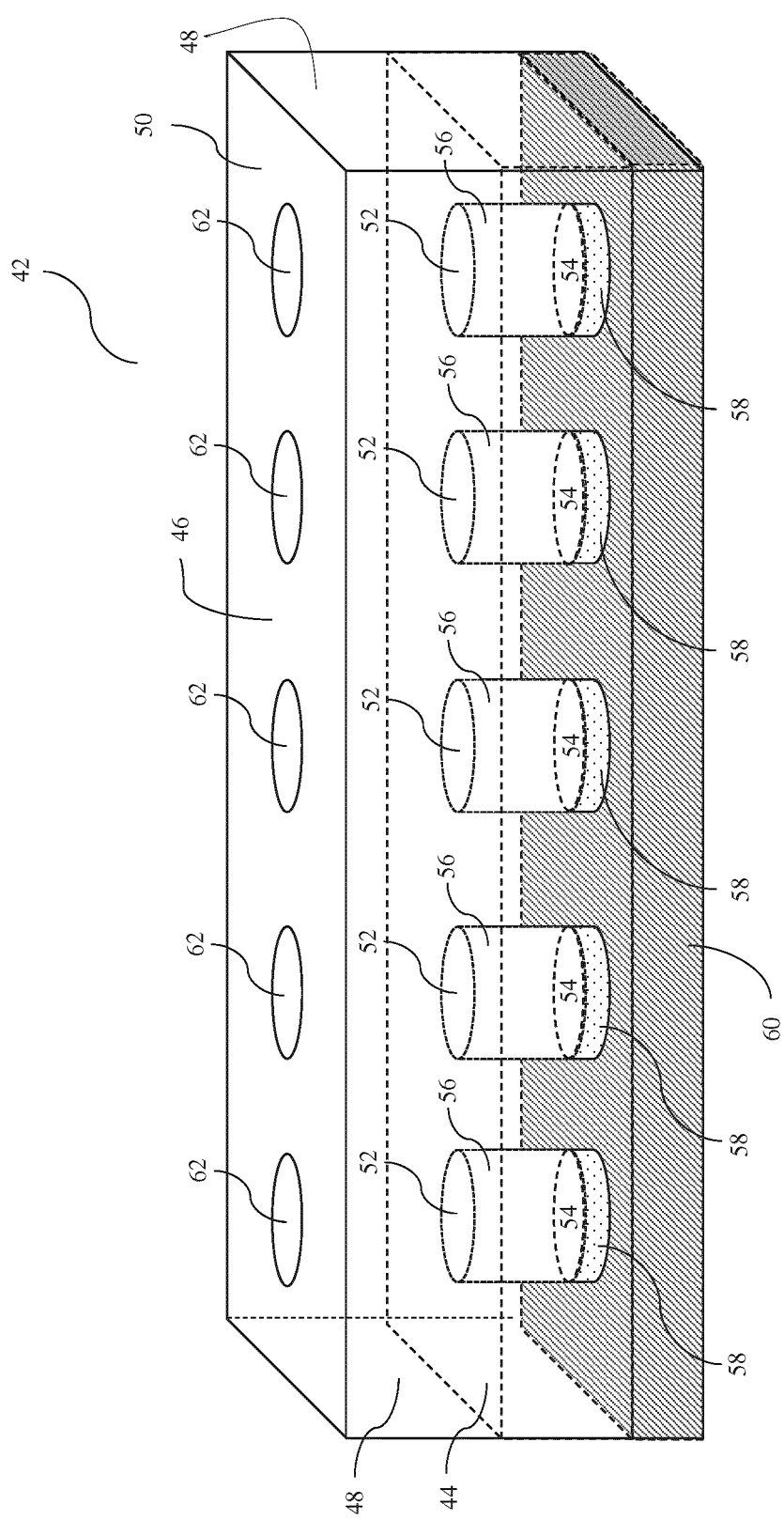
FIG. 2A shows a perspective view of a non-limiting example of a microchannel of a cell retention body of a microfluidic device as described herein.
Figure 2B:
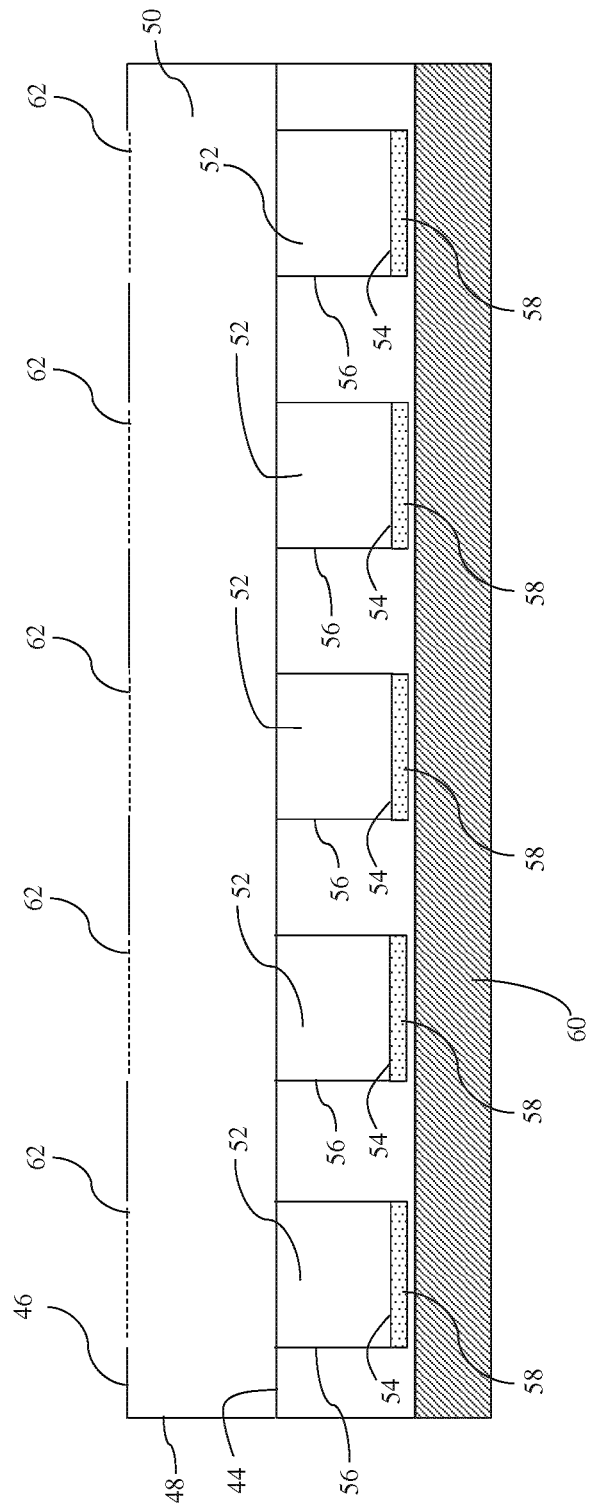
FIG. 2B shows a longitudinal cross sectional view of an example of a microchannel of a cell retention body of a microfluidic device as described herein.
Figure 2C:
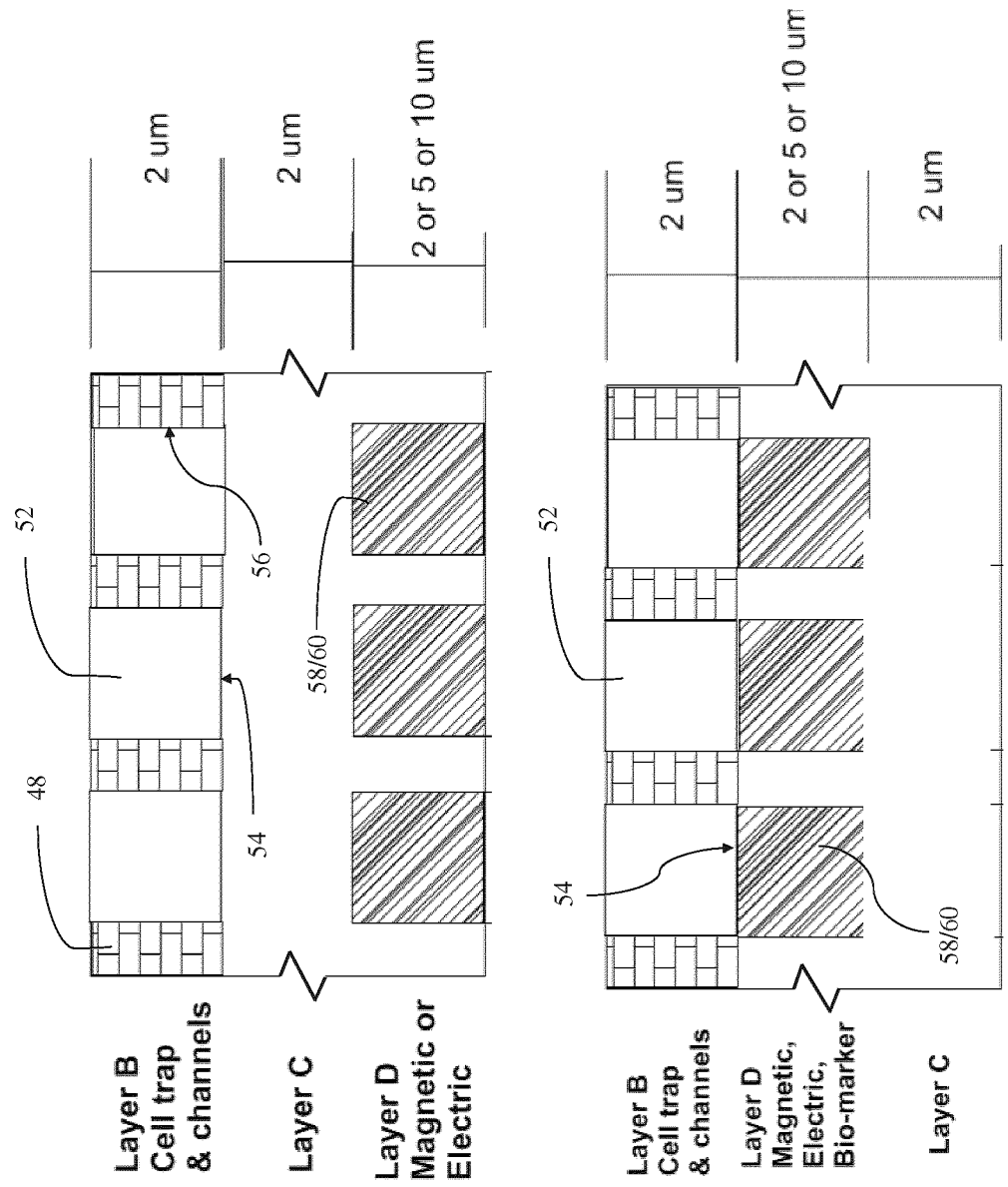
FIG. 2C shows a longitudinal cross sectional view of a portion of an example of a microchannel of a cell retention body of the microfluidic device as described herein. Upper panel: metallic film (58) is separated from the base of the sample well base (54) by a layer (C), the width of layer C in this non-limiting example is 2 μm; Lower panel: the metallic film (58) forms the sample well base (54), and layer (C) lies below the metallic film (58). In this non-limiting example the width of layer (C) is 2 μm.
Figure 2D:
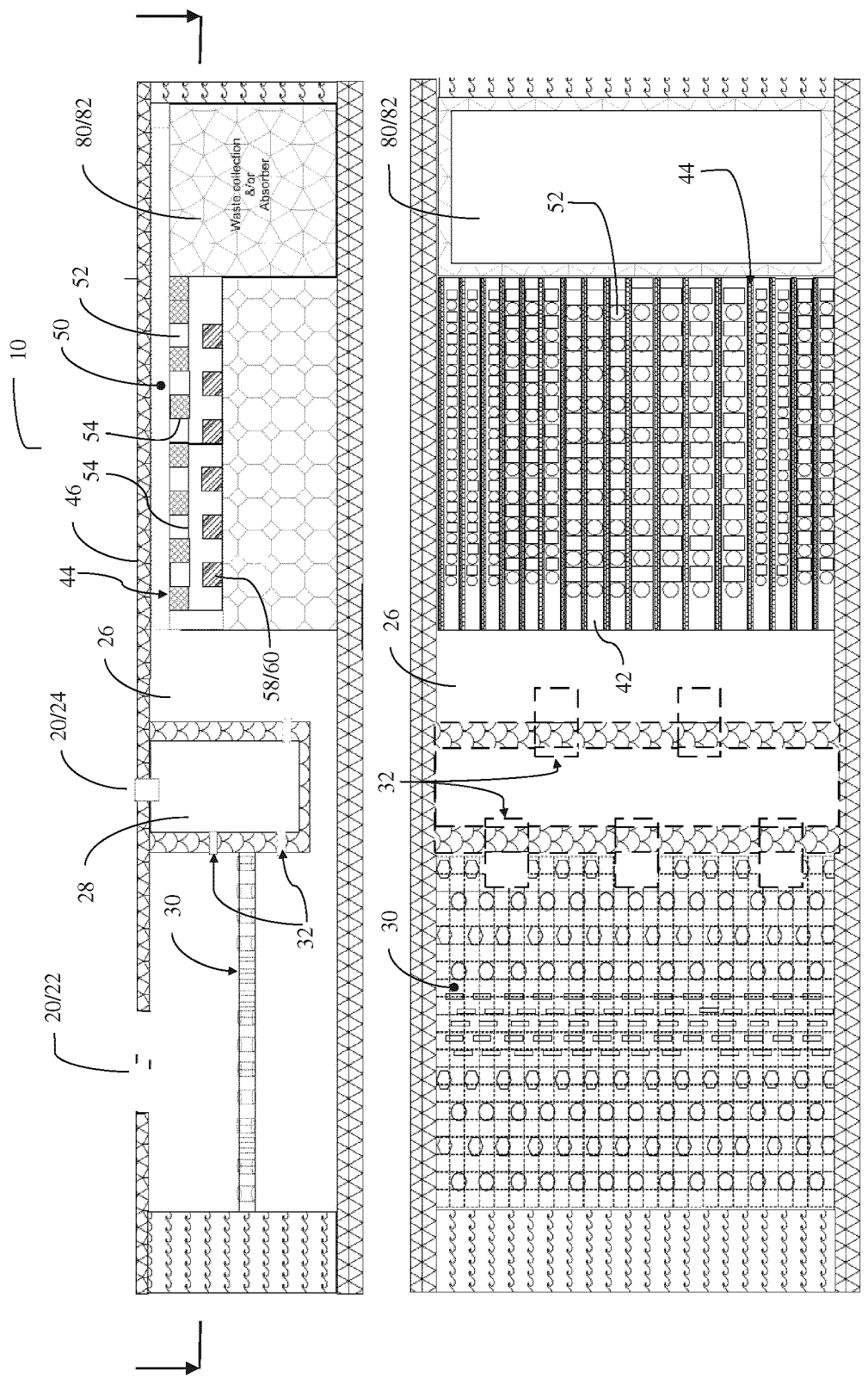
FIG. 2D upper panel: shows a longitudinal cross sectional view of a non-limiting example of a microfluidic device (10) described herein. Lower panel: is a cross sectional top view, along the arrows indicated in the upper panel, of the microfluidic device (10).
Figure 2E:
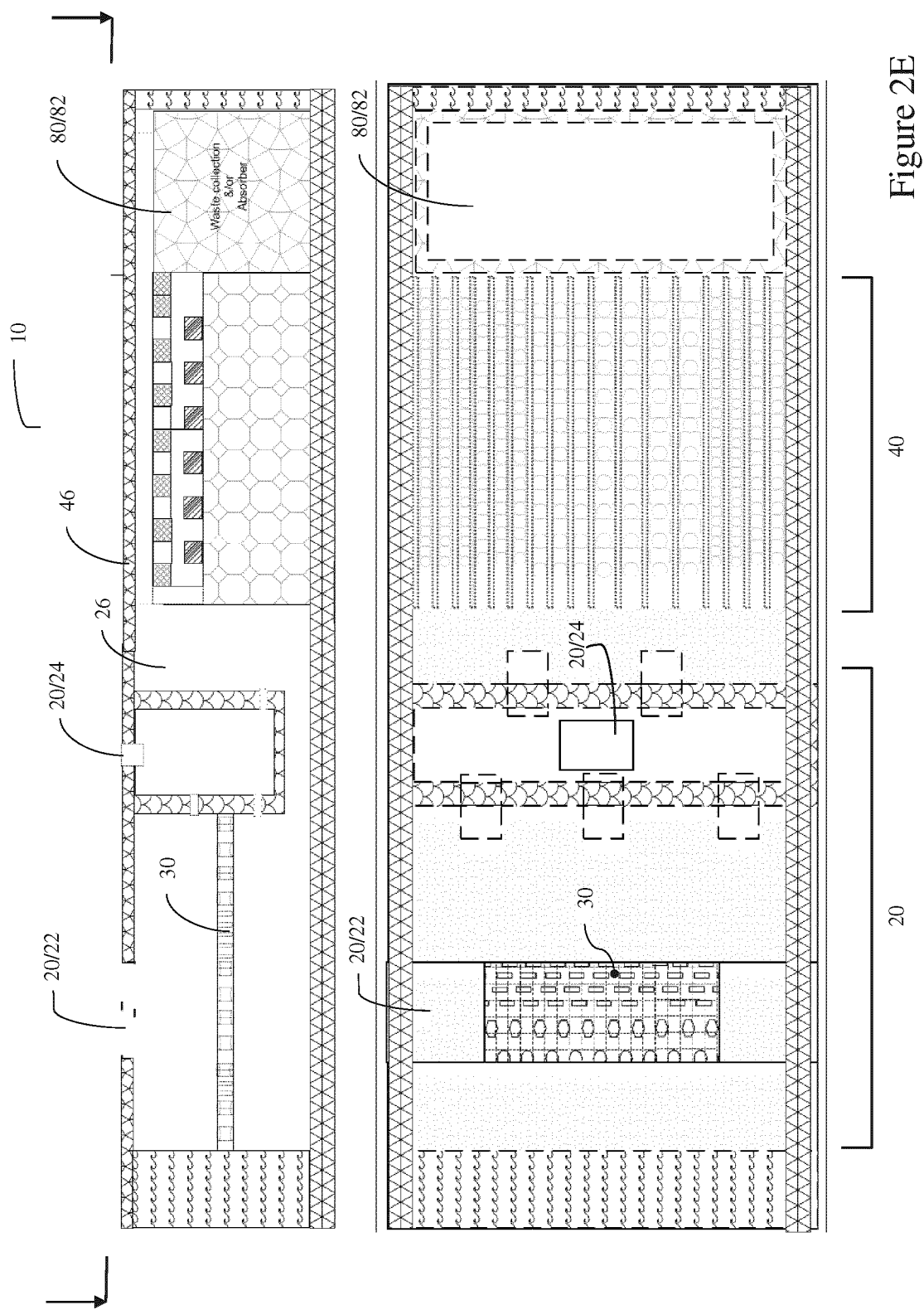
FIG. 2E upper panel: shows a longitudinal cross sectional view of a non-limiting example of a microfluidic device (10) described herein. Lower panel: is a top view, along the arrows indicated in the upper panel, of the microfluidic device (10).

The sample inlet 20 may also comprise a mixing chamber 26, for example as shown in FIGS. 1A, 2D and 2E, within which the sample mixes with the optional diluent before entering into the cell retention body 40. Alternatively, the sample inlet may comprise a single opening for receiving a diluted sample of blood that has already been pre-mixed with diluent (for example as shown in FIG. 1B). If the diluent is added to a separate chamber 28 (FIGS. 2D and 2E), then the diluent exits this chamber via ports 32 to mix with the sample in the mixing chamber 26. The diluent may also exit chamber 28 via port 32 and mix with the sample prior to the samples passage through filter 30.

The optional cell selective filter 30 may be any type of filter including a filter that separate cells and other components in the sample based on size of the components, or the filter may separate cell and other components in the sample based on ionic properties of the components, or a combination thereof. There may be one or multiple layers of filters, for example, one to five layers of filters or any amount therebetween. If multiple filters are used, then each filter may be placed on top of each other with or without a space between each filter, or the filters may be offset with respect to the other filters thereby permitting some or all of the sample to pass though the filters. The one or more filter 30 may be positioned within the mixing chamber of the microfluidic device 10 either horizontally (along the same plane as the cell retention body 40) and spanning the width and length of mixing chamber 26 (e.g. as shown in FIG. 2D), horizontally but not spanning the entire width or length of the mixing chamber 26 so that the filters are off-set with respect to each other, or the filters may be off-set and positioned at an angle with respect to the cell retention body 40. Other arrangement of the filters within the mixing chamber 26 may also be used. For example, filter 30 may be located along (i.e. co-planar with), or above, the plane of the lower first wall 44 of microchannel 42, or the filter 30 may be located along (i.e. co-planar with), or above, the plane of upper level of the cell retention body 40, so that the flow of the sample into the chamber may be assisted by gravity.

If the filter separates the sample components based on size exclusion, then the size and shapes of the pores of the filter may vary, for example as shown in FIG. 1E. In this non-limiting example, the pores of a size exclusion filter may be circular, elongated, polygon, for example hexagonal, square, octagonal or other shape, or a combination thereof. The size (diameter) of the pores of the size exclusion filter may range from about 1 µm to about 20 µm or any amount therebetween. For example, the size (diameter) of the pores may range from about 1, 2, 3, 4, 5, 6, 7, 8, 9, 10, 11, 12, 13, 14, 15, 16, 17, 18, 19, 20 µm or any amount therebetween. If elongate, size of the pores of the size exclusion filter may range in length from about 5 µm to about 20 µm or any amount therebetween, and the width may range from about 1 µm to about from 5 µm. For example, an elongate pore may range from about 1 µm by 5 µm, to about 5 µm by 20 µm or any amount therebetween, for example 1 µm by 10 µm, 2 µm by 10 µm, 3 µm by 12 µm, 4 µm by 15 µm, or 5 µm by 20 µm, or any amount therebetween.

If the microfluidic device 10 incorporates one or more filter 30, then the sample may be introduced into sample inlet 20 under pressure to ensure that the sample passes through filter 30 and enters the cell retention body 40. Alternatively, a vacuum may be exerted at collection reservoir 80 in order to encourage the sample to pass through filter 30 and enter cell retention body 40. Furthermore, the sample may be introduced into the microfluidic device 40 under pressure, and a vacuum may be applied (at collection reservoir 80) in order for the sample to pass through filter 30 and enter cell retention body 40. Alternatively, a vacuum, or suction, may be applied via a vacuum port positioned at or near the collection reservoir 80, or the vacuum port may be positioned at the distal end of the microchannel 42, opposite to the inlet 20.

The sample may be pre-treated prior to introduction into the sample inlet 20. For example, the sample may be diluted prior to introducing the sample into the sample inlet 20, the sample may be pretreated (e.g. pre-filtered) to remove large components. For example, if the sample is a blood sample, then white blood cells and other large debris may be removed prior to introducing the sample into the sample inlet 20, or a combination thereof.

The use of a filter 30 within the microfluidic device 10 is optional. For example, the sample to be added to the microfluidic device 10, may be pre-filtered and introduced into the microfluidic device via sample inlet 20. In such as case, there may be no need for further filtration of the sample within the device, and the microfluidic device 10 may not comprise filter 30.

If the microfluidic device is not to be disposed of after use, then, the sample inlet 20 may also include one or more than one washout port (not shown) that is in fluid communication with the sample inlet 20, or in fluid communication with the sample inlet 20 and the microchannels 42, so that after a sample has been analyzed, the sample inlet 20, or the sample inlet 20 and the microchannels 42, may be washed if desired to remove traces of the sample from the microfluidic device 10 in preparation for the next sample.

Figure 3:
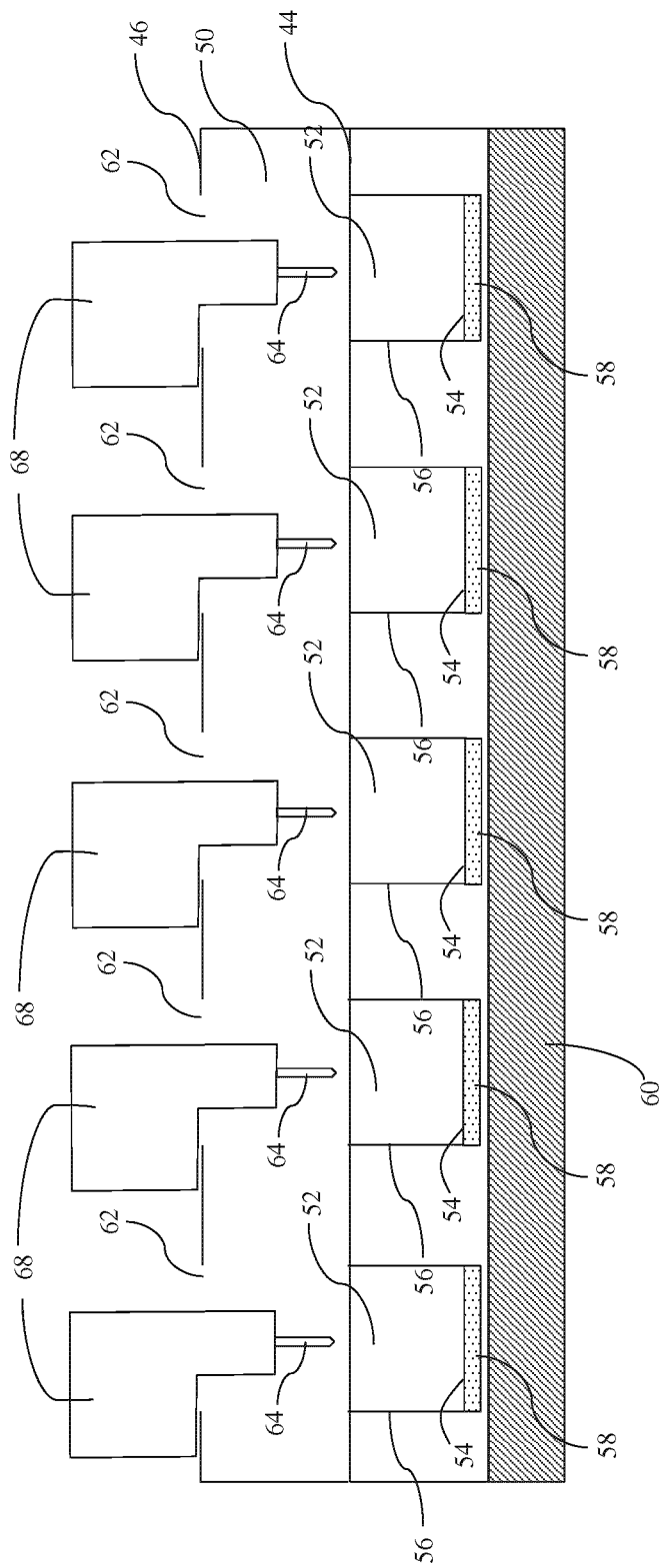
FIG. 3 shows a longitudinal cross-section side view of an example of a microchannel accommodating a measurement system (68) comprising for example, an indenter (64) in the openings of the upper second wall (46).
Figure 4:
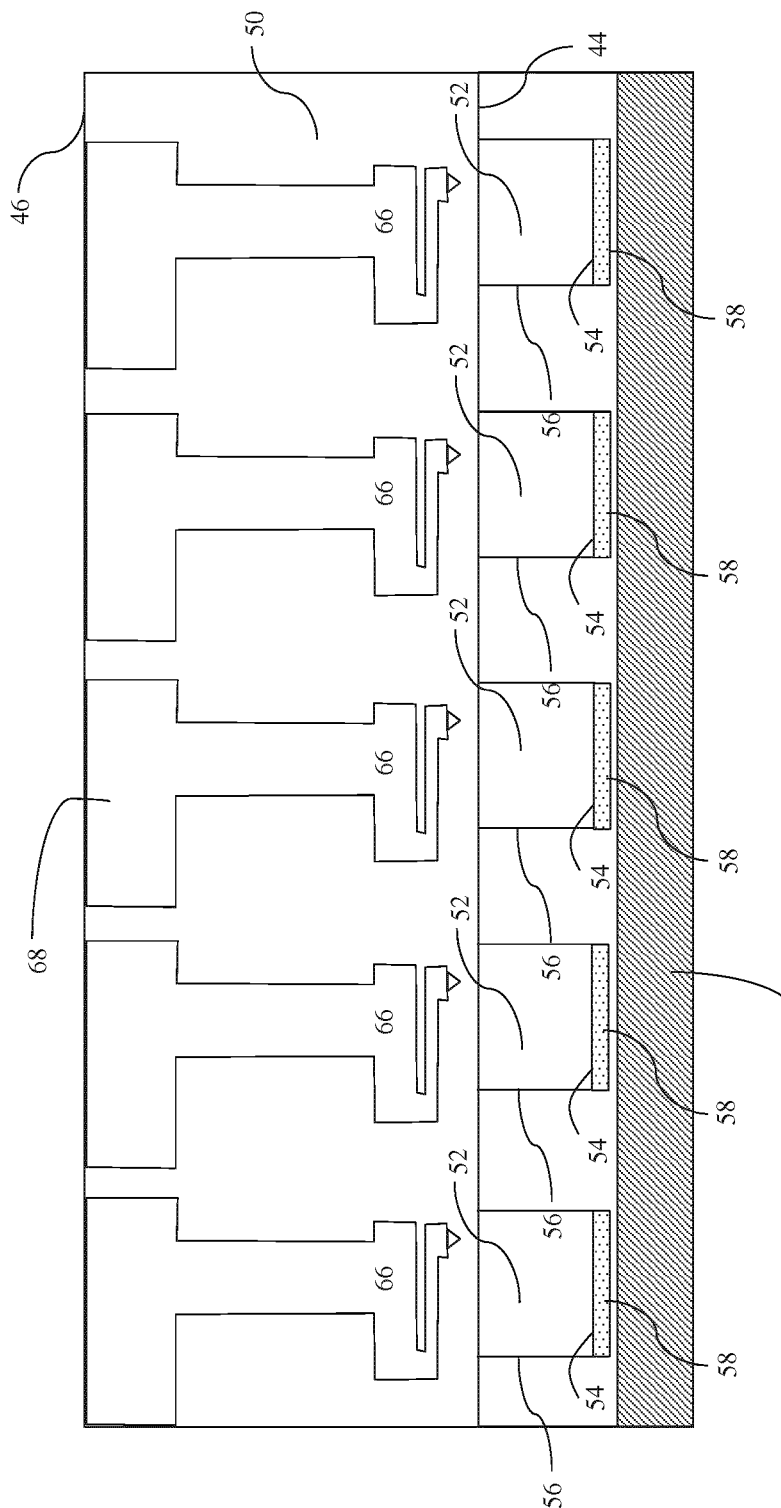
FIG. 4 shows a longitudinal cross-section side view of an example of a microchannel accommodating a measurement system (68) comprising for example, a piezoresistive cantilever (66) in the openings of the upper second wall (46).

The cell retention body 40 of the microfluidic device 10 comprises one or more than one microchannel 42, each of which may be curved or linear as desired, in fluid communication with the sample inlet 20. For example, the cell retention body 40 may comprise from about 1 to about 500 microchannels 42, or any amount therebetween. For example, 1, 2, 4, 6, 8, 10, 15, 20, 25, 30, 35, 450, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500 microchannels, or any amount therebetween. With reference to FIGS. 2A and 2B, each of the one or more than one microchannel 42 is further comprised of a lower first wall 44, an optional upper second wall 46, and side walls 48, which together define a microchannel volume 50 through which the sample, for example a diluted blood sample, passes. The dimensions of the microchannel volume 50 may be set to physically restrict the type or types of cells that may be carried through the one or more microchannel 42. For example, height of side wall 48 (i.e. extending from the lower first wall 44 to the optional upper second wall 46) may be between about 1.0 µm to about 30.0 µm, or any amount therebetween, for example, 1.0, 1.2, 1.4, 1.6, 2.0, 2.2, 2.4, 2.6, 2.8, 3.0 3.2, 3.4, 3.6, 3.8, 4.0, 4.2, 4.4, 4.6, 4.8, 5.0, 5.5, 6.0, 6.5, 7.0, 7.5, 8.0, 8.5, 9.0, 9.5 10.0, 12, 14, 16, 18, 20, 22, 24, 25, 26, 27, 28, 29, 30 µm, or any amount therebetween. The height that is selected may selectively permit passage of red blood cells (RBCs) through the one or more microchannel 42 while restricting the passage of larger white blood cells (WBCs). Other dimensions of the side wall height 48 and the microchannel 42 may be selected based upon the cell type to be separated. The dimensions of the microchannel volume 50 may also function to physically restrict the spatial orientation of cells passing through the one or more microchannel 42. For example, side walls 48 having a height between about 1.0 µm and about 10.0 µm or any amount therebetween, may restrict passage within the microchannel 42 to those RBCs being in a substantially "flat" orientation. However, an increased height of side wall 48 may be desired in order to accommodate large probes of a measurement system 68 that may be used to determine a property of an immobilized cell, for example, side walls 48 having a height between about 1.0 µm and about 30.0 µm or any amount therebetween. Examples of measurement systems 68, which are not to be considered limiting, may comprise an indenter 64, or a piezoresistive cantilever 66 (FIGS. 3 and 4). As described herein, other measurement systems 68 may be used in conjunction with microfluidic device 10.

As shown in FIGS. 1C, 1D, 2D and 2E, the one or more than one microchannels 42 within the cell retention body 40 may vary in width. For example the width of the microchannel 42 may range from 8 µm to about 30 µm or any amount therebetween. For example, the width of the microchannel 42 may be 8, 9, 10, 11, 12, 13, 14, 15, 16, 17, 18, 19, 20, 22, 24, 26, 28, 30 µm or any amount therebetween.

The lower first wall 44, the upper second wall 46, and side walls 48 may be made of any suitable hydrophilic or hydrophobic material in order to provide a surface to facilitate capillary movement of the sample through the microchannel 42. The microchannel may be comprised of any biocompatible materials, for example, a glass material such as a borosilicate glass (e.g. BOROFLOAT® glass; Corning 0211 or 7740), a biocompatible polymeric material, a polycarbonate material, polytetrafluoroethylene (e.g. TEFLON®), stainless steel, silicon, graphene, graphene spiked with metallic or conductive components, and the like, or a surface coated with silver, or gold, or a surface coated using chemical vapor deposition of synthetic diamond or other suitable material, or the like.

The lower first wall 44 comprises one or a plurality of sample wells 52 along the length of the microchannel 42. For example, the lower first wall may comprise from about 1 to about 10,000 or any amount therebetween, sample wells. For example, 1, 5, 10, 15, 20, 25, 30, 35, 40, 50, 75, 100, 150, 200, 250, 300, 240, 400, 500, 600, 700, 800, 900, 1,000, 5,000, 10,000 sample wells, or any amount therebetween. As shown in FIGS. 1C, 1D, 2D and 2E, the sample wells 52 may vary in diameter within the cell retention body 40. For example the diameter of the sample well 52 may range from 8 µm to about 30 µm or any amount therebetween. For example, the diameter of the sample well 52 may be 8, 9, 10, 11, 12, 13, 14, 15, 16, 17, 18, 19, 20, 22, 24, 26, 28, 30 µm or any amount therebetween. The shape of the sample well 52 may vary and comprise a cross section that is circular, oval, or polygonal, for example a square, hexagonal, octagonal and the like.

Each of the one or plurality of sample wells 52 comprises: a sample well base 54, one or more sample well side wall 56, and a metallic film 58 positioned on or below the sample well base 54. For example, each sample well base 54 may be circular or polygonal in shape with a diameter between about 8.0 µm and 30.0 µm, or any amount therebetween, for example, 8.0, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 12.2, 12.4, 12.6, 12.8, 13.0, 13.2, 13.4, 13.6 13.8, 14.0, 14.2, 14.4, 14.6, 14.8, 15.0, 15.2, 15.4, 15.6, 15.8, 16.0, 16.2, 16.4, 16.6, 16.8, 17.0, 17.2, 17.4, 17.6, 18.0, 18.2, 18.4, 18.6, 18.8, 19.0, 19.2, 19.4, 19.6, 19.8, 20.0, 20.5, 21.0, 21.5, 22.0, 22.5, 23.0, 23.5, 24.0, 24.5, 25.0, 26.0, 27.0, 28.0, 29.0, 30 µm, or any amount therebetween, and the sample well side wall 56 may have a height between about 1.0 µm and 10.0 µm, or any amount therebetween, for example, 1.0, 1.2, 1.4, 1.6, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10.0 µm, or any amount therebetween. The shape and dimensions of the sample well 52 assist in facilitating the isolation of single cells, for example, a RBC, within each well. FIGS. 2A and 2B show sample wells 52 having side walls 56 perpendicular to the sample well base 54, however, the side walls may be curved or positioned at an angle relative to the sample well base 54. In this way, the physical dimensions of each sample well is such that only a single cell may be accommodated within each well.

As shown in FIGS. 2A, 2B, 2C, 2D, 3, and 4, a metallic film 58, a magnet 60, or both a metallic film and a magnet (58/60), may be positioned on or below the sample well base 54.

If a metallic film 58 is positioned on or below the sample well base 54, then the metallic film may be comprised of a magnetic metal, such as nickel, cobalt, neodymium-iron-boron, however, other metals may also be used, for example, stainless steel, copper, platinum, niobium-iridium-iron, graphene, graphene spiked with metallic or conductive components, silver, gold, and the like. The metal film may be applied by chemical vapor deposition, sputtering or electroplating, in combination with lithography (mask) and etching to position the metal film below the sample well base. Alternatively, the metallic film may be inserted within, or placed below, the sample well base 54. The amount of metallic film to be inserted within, or placed below the sample well base 54 may be readily determined by one of skill in the art, and may depend upon the sample flow rate through the microchannels 42, the thickness of, or material comprising, the sample well base 42, or the type of sample that is being applied to the microfluidic device.

Each metallic film positioned at each sample well base 54 may be in electrical communication with other metallic films positioned below respective a sample well base, and a current may be passed thought the metallic film 58 in order to magnetize the metallic film and assist in immobilizing single cells, for example RBCs, or cells comprising antibody-conjugated magnetic beads, within each sample well 52 based on the inherent magnetic properties of the RBCs or magnetically-conjugated cells. For example, a strip of graphene spiked with metallic or conductive components, or other magnetizable material may be placed under a series of sample wells 52 along the length of a microchannel 42, so that a current may pass through the strip. In these examples, lower wall 44 that separates sample wells 52, acts as an insulating layer so that cells, that are not localized within a sample well, and that are passing through the microchannel 42, are not magnetically immobilized outside of sample well 52.

Alternatively, a magnet 60 (that provides a magnetic field of about 0.15 T or greater), for example, a magnetized metal, a rare-earth magnet, a neodymium or a samarium based rare earth magnet and the like, may be positioned on or below each sample well base 54 in order to immobilizing single cells, for example RBCs, or cells comprising antibody-conjugated magnetic beads, within each sample well 52 based on the inherent magnetic properties of the RBCs or magnetically-conjugated cells. Additionally, an induction coil, or other magnetic-field-generating device, may be placed below each sample well so that a magnetic field is generated by the induction coil or magnetic-field-generating device when a current is applied to the induction coil or magnetic-field-generating device. As a result, a cell, for example a RBC, is attracted to, and immobilized on, the sample well base 54 by virtue of the inherent magnetic properties of RBC, attributed to their iron-containing hemoglobin content.

In another example, a magnet 60 may be positioned below each sample well base 54 that comprises a metallic film 58 (e.g. FIGS. 2A, 2B, 3, 4). In this example, the magnet 60 provides a magnetic field of about 0.15 T or greater, which is concentrated by the metallic film 58. The concentrated magnetic field assists in immobilizing single cells, for example RBCs, or cells comprising antibody-conjugated magnetic beads, within each sample well 52 based on the inherent magnetic properties of the RBCs or magnetically-conjugated cells. For example, a rare-earth magnet, for example a neodymium or a samarium based rare earth magnet, an induction coil, or other magnetic-field-generating device, may be placed below the sample well, so that the metallic film 58 concentrates the magnetic field generated by the magnet, induction coil or magnetic-field-generating device. As a result, a cell, for example a RBC, is attracted to, and immobilized on, the sample well base 54 by virtue of the inherent magnetic properties of RBC, attributed to their iron-containing hemoglobin content.

If magnet 60 is used to magnetize metallic film 58, then the magnet may be provided as a layer and may be integrally formed with and positioned under, the cell retention body 40 (for example as shown in FIGS. 2A, 2B, 3 and 4). Alternatively, magnet 60, may be provided as a removable layer and may be positioned under the cell retention body 40, comprising metallic films 58, as desired. In this way, the cell retention body 40 may be placed on top of magnet 60 when immobilization of cells is required. In either situation that uses a magnet as a layer, lower wall 44 that separates sample wells 52, acts as an insulating layer so that cells, that are not localized within a sample well, and that are passing through the microchannel 42, are not magnetically immobilized outside of sample well 52.

Single cells may also be immobilize within sample wells 52 by coating sample well bases 54 with cell-specific binding molecules, such as antibodies, glycoprotein-binding lectins, receptor binding antigens and the like. The coated sample well base 54 may be used alone, or in conjunction metallic film 58. For example, if the cells to be separated do not comprise an inherent, or an introduced magnetic property (e.g. no conjugated magnetic beads) to assist in separation and collection, within the sample well 52, then the sample well 52 may be coated with cell-specific binding molecules, and the magnetic film 58, the magnet 60, or both need not be present, or if they are present, they be optionally used. For example, in addition to the size of the sample well 52 that assists in the size selection of a cell, cells may be further selected and immobilized within sample wells 52 using both biochemical (e.g. specific binding molecules) and magnetic properties, only biochemical properties, or only magnetic properties.

Figures 5A, 5B, 5C:
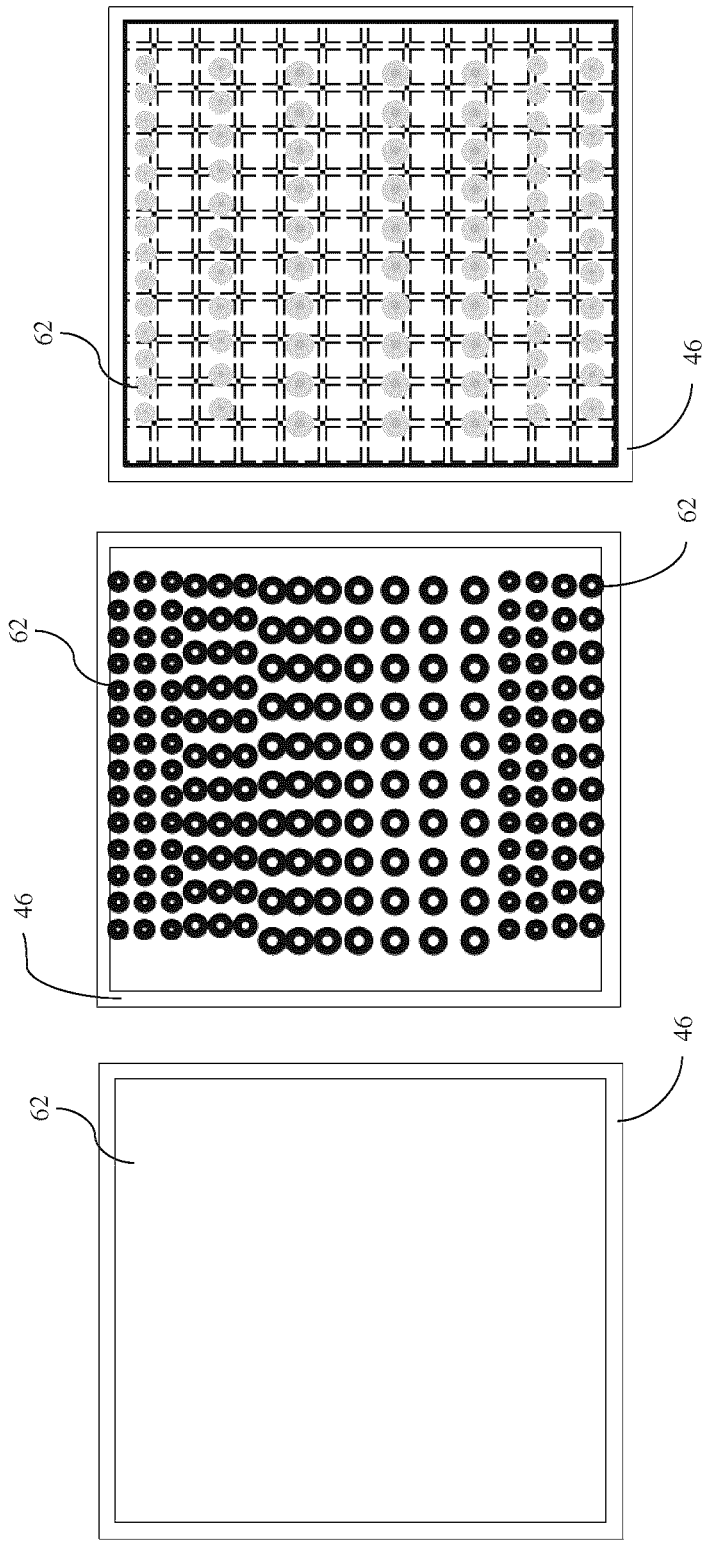
FIG. 5A shows a top view of an example of an upper second wall (46) defining opening (62). The opening defined by the upper wall may be fitted with a glass or polymeric coverslip; the glass or polymer coverslip may comprise one or more than one lens to assist a measurement systems, for example, a camera or a foldscope in optically analyzing the sample wells positioned below the upper second wall.
FIG. 5B shows a top view of an example of an upper second wall (46) defining a series of openings (62) that are of a shape, size, position that are in alignment with a corresponding set of like-sized, shaped and positioned sample wells located directly below the openings (52) defined by the upper second wall.
FIG. 5C shows another example of an upper second wall (46) defining a series of openings (62) that are positioned, and of a shape and size, so that they are in alignment with a corresponding set of like-sized and positioned sample wells located directly below the openings defined by the upper second wall.

The upper second wall 46 may be open as shown in FIG. 5A, or the upper second wall 46 may comprise a plurality of openings 62 in spatial alignment, and positioned above, each of the one or more than one sample wells 52 (FIGS. 5B, 5C). Each of the openings may be of a size to accommodate a measurement system 68 that is used to determine a property of the cell within the sample well 52.

The measurement system may include but is not limited, to an observation probe, an optical microscope, a proximity surface probe, a near-surface probe having nanometer-or micron scale resolution, a displacement probe, a magnetic probe, a load sensor probe, a thermal-probe, a scanning probe-based microscope (SPM), an atomic force microscope (AFM), a sliding AFM probe, a torsion or lateral force microscope, a cantilever based probe, a piezoresistive cantilever, a digital camera, or an indenter. The measurement system may be used for measuring one or more than one physical or biochemical property, for example, an electrical property, an electrical conductivity, an electrical resistivity, a magnetic property, an acoustic property, a mechanical property, an elastic property, a viscoelastic property, a viscosity property, a shear force property, a torsion property, a hardness property, an optical property, a thermal property, pH, or a combination of one or more of the properties of a cell, or a membrane of a cell located within the one or more than one sample well.

If the microfluidic device 10 does not comprise the optional second wall 46, then the measurement system 68 is positioned above, and in spatial alignment with, the one or more than one sample well 52, so that the measurement system 68 may have direct access to the one or more than one sample well. For example, when a cell has been immobilized within one or more sample wells 52, physical properties or measurements, biochemical properties or measurements, or both physical and biochemical properties or measurements of the cell or the cell membrane may be obtained using measurement system 68.

If the microfluidic device 10 comprises the upper second wall 46 then the upper second wall defines a series of openings 62 that are in spatial alignment with, the one or more than one sample well 52, so that the measurement system 68 positioned above the sample well 52 may have access to a cell within the sample well. For example, when a cell has been immobilized within one or more sample wells 52, physical properties or measurements, biochemical properties or measurements, or both physical and biochemical properties or measurements of the cell or the cell membrane may be obtained using measurement system 68.

Alternatively, the optional upper second wall 46 may not define any openings but rather the upper second wall may have one or more than one measurement system 68, for example a probe, mounted thereon. Each of the one or more than one probes is arranged to be in spatial alignment with each of the one or more than one sample well 52 to facilitate obtaining properties or physical measurements of the immobilized cell.

If the microfluidic device 10 comprises the optional upper second wall 46, then the upper second wall may be removable from the microfluidic device 10 to allow access to the microchannels 42. Alternatively, the upper second wall 46 may be integral with the microfluidic device 10 and be non-removable.

As shown in FIG. 3, each of the one or plurality of openings 62 may accommodate a measurement device 68, for example but not limited to an indenter 64. The alignment of the openings 62 above each of the one or plurality of sample wells 52 facilitates the direct access of the measurement device 68 with the immobilized cell, or membrane of the immobilized cell. If the measurement device 68 is an indenter 64, then the physical property obtained may include a membrane rigidity measurement. Any suitable indenter or piezoresistive cantilever may be used. If a piezoresistive cantilever is used, then the cantilever length may be from about 50 to about 250 µm, or any amount therebetween, for example a length of 50, 60, 70, 80, 90, 100, 120, 140, 160, 180, 200, 220, 240, 250 µm, or any amount therebetween.

FIG. 4 shows another example of the microfluidic device 10 wherein the measurement system 68 is a piezoresistive cantilever 66. In this example, each piezoresistive canitlever is fully contained within the microchannel volume 50 and is suspended from the upper second wall 46 in spatial alignment with each of the sample wells 52. The piezoresistive cantilever comprises a cantilever length of from about 50 to about 250 µm, or any amount therebetween, for example a length of 50, 60, 70, 80, 90, 100, 120, 140, 160, 180, 200, 220, 240, 250 µm, or any amount therebetween.

A shown in FIGS. 1A, 1B, 2D and 2E each of the one or more than one microchannels 42 may be in fluid communication with an optional collection reservoir 80 for collection of flow-through fluid and non-retained cells. In this example, fluid may be drawn into the collection reservoir 80 by means of suction, surface tension, or capillary force generated by an absorber 82. However, the use of a collection reservoir 80 is optional and it is not required for use of the microfluidic device 10 described herein. If desired, a vacuum, or suction, may be applied to the microchannels 42 via a vacuum port positioned at, or near, the collection reservoir 80.

Therefore, a microfluidic device is described herein. The microfluidic device comprises a sample inlet, an optional filter, and a cell retention body, the cell retention body comprising one or more than one microchannel in fluid communication with the sample inlet. Each of the one or more than one microchannel comprises a lower first wall, an upper second wall, and side walls, the lower first, an optional upper second and side walls defining a microchannel volume. The lower first wall comprises one or more than one sample well along a length of the microchannel. Each of the one or more than one sample well comprises a sample well base, one or more than one sample well side wall and a metallic film, or magnet, positioned on or below the sample well base. The optional upper second wall may define one or more than one opening so that each of the one or more than one opening is in spatial alignment, and positioned above, each of the one or more than one sample well.

Furthermore, a method of separating one or more than one target cell from a sample is provided. The method comprises applying a magnetic field to a microfluidic device, the microfluidic device comprising a sample inlet, an optional filter, and a cell retention body, the cell retention body comprising one or more than one microchannel in fluid communication with the sample inlet, each of the one or more than one microchannel comprises a lower first wall, an optional upper second wall, and side walls, the lower first, optional upper second and side walls defining a microchannel volume, the lower first wall comprises one or more than one sample well along a length of the microchannel, each of the one or more than one sample well comprises a sample well base, one or more than one sample well side wall and a metallic film, positioned on or below the sample well base, the optional upper second wall may define one or more than one opening so that each of the one or more than one opening is in spatial alignment, and positioned above, each of the one or more than one sample well, and introducing the sample containing the one or more than one target cell into the sample inlet of a microfluidic device and permitting the sample to flow along the one or more than one microchannel, the metallic film concentrating the applied magnetic field within the one or more than one sample well, so that one of the one or more than one target cell is retained, by cell size and magnetic property, within the one or more than one sample well, thereby separating the one or more than one target cell from the sample and producing a separated target cell.

Also provided is a method of separating one or more than one target cell from a sample. The method comprises introducing the sample containing the one or more than one target cell into a sample inlet of a microfluidic device, the microfluidic device comprising the sample inlet, an optional filter, and a cell retention body, the cell retention body comprising one or more than one microchannel in fluid communication with the sample inlet, each of the one or more than one microchannel comprises a lower first wall, an optional upper second wall, and side walls, the lower first, optional upper second and side walls defining a microchannel volume, the lower first wall comprises one or more than one sample well along a length of the microchannel, each of the one or more than one sample well comprises a sample well base, one or more than one sample well side wall and a magnet, positioned on or below the sample well base, the optional upper second wall may define one or more than one opening so that each of the one or more than one opening is in spatial alignment, and positioned above, each of the one or more than one sample well, and permitting the sample to flow along the one or more than one microchannel so that one of the one or more than one target cell is retained based on cell size and magnetic property, within the one or more than one sample well, thereby separating the one or more than one target cell from the sample and producing a separated target cell.

The microfluidic device as described herein may be used along with a measurement system, for example, an apparatus that comprises cameras, probes or cantilever probes in order to analyze the one or more separated and immobilized cells. For example, which is not to be considered limiting, the measurement system may be a scanning probe microscope (SPM; see for example, Bharat Bhushan and Othmar Marti, "Scanning Probe Microscopy—Principle of Operation, Instrumentation, and Probes", Chapter 2, pg 37-110, in B. Bhushan (ed.), *Nanotribology and Nanomechanics*, DOI 10.1007/978-3-642-15283-2_2, # Springer-Verlag Berlin Heidelberg 2011; M S Ramachandra Rao and G Margaritondo, J. Phys. D: Appl. Phys. 44 (2011) 460301 (2pp) doi:10.1088/0022-3727/44/46/460301; G. Friedbacher, H. Fuchs, 1999, Pure Appl. Chem., Vol. 71, No. 7, pp. 1337-1357; which are incorporated herein by reference). Non-limiting examples of a scanning probe microscope that may be used in conjunction with the microfluidic device include a NanoSurf AFlexAFM, Bruker Multimode 8, or an Asylum Research MFP 3D Origin AFM, CSM.

The measurement system may also determine viscoelastic properties of immobilized cells for example, using the method of Ngana and Tang ("Response of power-law-viscoelastic and time-dependent materials to rate jumps", A. H. W. Ngana and B. Tang, pg. 853-862, J. Mater. Res., Vol. 24, No. 3, Mar 2009, which is incorporate herein by reference). Physical properties of a cell or cell membrane may be determined using atomic force microscope (see for example, Israelachvili J., "*Intermolecular and Surface Forces*", Academic Press (1985-2004), ISBN 0-12-375181-0; B. Cappella, G. Dietler, :Force-distance curves by atomic force microscopy", Surface Science Reports 34 (1999) 1-104; Hans-Jurgen Butt, Brunero Cappella, Michael Kappl, "Force measurements with the atomic force microscope: Technique, interpretation and applications" Surface Science Reports 59 (2005) 1-152; which are incorporated herein by reference). Furthermore, indentation of a cell may be determined using AFM (see for example US 2010/0039919; US 20150047078; P. Vettiger, et. al., The "Millipede" Nanotechnology Entering Data Storage, IEEE transactions on nanotechnology, Vol. 1, No. 1, MARCH 2002, 39-55; which are incorporated herein by reference).

Additionally, an optical beam deflection apparatus may be used to measure cantilever deflection (Dukic M., et al. 2015, Scientific Report 5: art No 16393; Putman, C A J et al, 1992; which are incorporated herein by reference).

Alternatively, for biochemical determinations, for example ELISA analysis, or enzymatic reactions, spectrophotometric or colour-based analysis, the microfluidic device as described herein may be used in conjunction with a microplate reader, or an absorbance/spectrometer microplate reader, for example, but not limited to, those available from Azure Biosystems Inc, Molecular Devices LLC, Bio-Rad, BioTek Instruments, and the like. The dimensions of the microfluidic device described herein would be adjusted accordingly to operate with the desired microplate reader.

A method of determining a property of a cell is also described. This method comprises, producing a separated target cell by the method as described herein, and determining a physical property measurement of the separated target cell or a membrane of the separated target cell, the property selected from an electrical property, an electrical conductivity, an electrical resistivity, a magnetic property, an acoustic property, a mechanical property, an elastic property, viscoelastic property, a viscosity property, a shear force property, a torsion property, a hardness property, an optical property, a thermal property, or a combination thereof, using for example, but not limited to, a scanning probe-based microscope (SPM), an atomic force microscope (AFM), a torsion or lateral force microscope, a sliding AFM probe, an observation probe, a proximity surface probe, a near-surface probe, a displacement probe, a magnetic probe, a load sensor probe, a thermal probe, a digital camera, and an indenter. The SPM may comprise a probe for measuring changes in electrical conductivity and resistivity under mechanical strain of the separated target cell. The AMF may comprise a piezoresistive cantilever for measuring changes in electrical conductivity and resistivity under mechanical strain of the separated target cell. Alternatively, the separated target cell may be analyzed biochemically, for example by ELISA, enzymatic reactions; receptor assays, or other biochemical assays. The target cell may also be processed as required prior to the biochemical analysis, for example, adding buffer or other reagent to the sample well, altering the pH within the sample well, or the target cell may be lysed prior to biochemical analysis.

For example, a method of determining a property of a cell may comprise producing a separated target cell by the method described above, and determining an elastic modulus measurement of a membrane of the separated target cell using an atomic force microscope (AFM). The AMF may comprises an indenter for measuring hardness of a cell membrane of the separated target cell, or the AMF may comprise a piezoresistive cantilever for measuring changes in electrical conductivity and resistivity under mechanical strain of the separated target cell.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A microfluidic device comprising a cell retention body and a sample inlet located at a first end of the cell retention body, the cell retention body comprising one or more than one microchannel in fluid communication with the sample inlet, each of the one or more than one microchannel comprising a lower first wall and side walls, the lower first wall and the side walls defining a microchannel volume, the lower first wall comprising a plurality of sample wells along a length of the microchannel, each of the plurality of sample wells disposed below the lower first wall and comprising a sample well base, one or more than one sample well side wall, wherein a top of the sample well is aligned with a surface of the lower first wall, and a metallic film, or magnet, in alignment with, and positioned on or below the sample well base.

2. The microfluidic device of claim 1 further comprising an upper second wall, the upper second wall defining a plurality of openings so that each of the plurality of openings is in spatial alignment, and positioned above, each of the plurality of sample wells.

3. The microfluidic device of claim 2, wherein each of the plurality of openings of the upper second wall provides access for a measurement system to the plurality of sample wells.

4. A microfluidic device comprising a cell retention body and a sample inlet located at a first end of the cell retention body, the cell retention body comprising one or more than one microchannel in fluid communication with the sample inlet, each of the one or more than one microchannel comprising a lower first wall, an upper second wall, and side walls, the lower first, upper second and side walls defining a microchannel volume, the lower first wall comprising a plurality of sample wells along a length of the microchannel, each of the plurality of sample wells disposed below the lower first wall and comprising a sample well base, one or more than one sample well side wall, wherein a top of the sample well is aligned with a surface of the lower first wall, and a metallic film, or magnet, positioned on or below the sample well base, the upper second wall having one or more than one probe suspended thereto, so that each of the one or more than one probe is in spatial alignment, and positioned above, each of the plurality of sample wells.

5. The microfluidic device of claim 1, wherein the sample inlet comprises a first and second opening, the first opening for receiving a sample or portion thereof and the second opening for receiving a diluent, and a mixing chamber in which the sample is mixed with the diluent.

6. The microfluidic device of claim 1, wherein the sample inlet comprises one opening for receiving a diluted sample.

7. The microfluidic device of claim 1, wherein the sample inlet comprises a pre-loaded reservoir of diluent, one opening for receiving a sample, and a mixing chamber in which the sample is mixed with the diluent.

8. The microfluidic device of claim 1, wherein a cell selective filter is placed at or below the sample inlet, or the cell selective filter is placed in a mixing chamber.

9. The microfluidic device of claim 1, wherein the microchannel side walls have a height between about 1.0 μm and about 30.0 μm.

10. The microfluidic device of claim 1, wherein the sample well base is circular in shape with a diameter between about 8.0 μm and about 30.0 μm and the sample well side wall has a height between about 1.0 μm and about 10.0 μm.

11. The microfluidic device of claim 1, wherein the sample well base is circular in shape with a diameter between about 8.0 μm and about 30.0 μm and the sample well side wall is curved or sloped.

12. The microfluidic device of claim 1, wherein the metallic film is substantially comprised of nickel, cobalt, neodymium-iron-boron, platinum, silver or gold.

13. The microfluidic device of claim 1, wherein the sample well base is coated with cell-specific binding molecules.

14. The microfluidic device of claim 1, wherein a magnet, an induction coil or a magnetic field-generating device is below each of the plurality of sample wells.

15. The microfluidic device of claim 1, wherein the one or more than one microchannel is in fluid communication with a flow-through collection reservoir.

16. The microfluidic device of claim 15 wherein the flow through collection reservoir further comprises an absorber for generating suction.

17. A method of separating one or more than one target cell from a sample comprising applying a magnetic field to the microfluidic device of claim 1, introducing the sample into the sample inlet, and permitting the sample to flow along the one or more than one microchannel so that one of the one or more than one target cell is retained within the one or more than one sample well, thereby separating the one or more than one target cell from the sample to produce a separated target cell.

18. A method of determining a property of a cell comprising, producing a separated target cell by the method of claim 17, and determining one or more than one physical or biochemical property of the separated target cell, or a membrane of the separated target cell, the one or more than one physical or biochemical property selected from an electrical property, an electrical conductivity, an electrical resistivity, a magnetic property, an acoustic property, a mechanical property, an elastic property, a viscoelastic property, a viscosity property, a shear force property, a torsion property, a hardness property, an optical property, a thermal property, pH, or a combination thereof.

19. The method of claim 18 wherein the one or more than one physical or biochemical property is determined using scanning probe microscopy (SPM).

20. The method of claim 19 wherein the SPM comprises a cantilever probe for measuring changes in electrical conductivity and resistivity under mechanical strain, or magnetic, biochemical, or behavioral properties of the separated target cell.

21. The microfluidic device of claim 14, wherein the metallic film positioned on the sample well base concentrates a magnetic field generated by the magnet, induction coil or magnetic-field-generating device.

* * * * *